United States Patent [19]

Graetzel et al.

[11] Patent Number: 5,463,057
[45] Date of Patent: Oct. 31, 1995

[54] BI-PYRIDYL-RUMETAL COMPLEXES

[75] Inventors: Michael Graetzel, St-Sulpice; Mohammad K. Nazeeruddin, Chavannes, both of Switzerland

[73] Assignee: Ecole Polytechnique Federale de Lausanne, (EPFL), Switzerland

[21] Appl. No.: 211,824

[22] PCT Filed: Aug. 19, 1993

[86] PCT No.: PCT/EP93/02221

§ 371 Date: Apr. 20, 1994

§ 102(e) Date: Apr. 20, 1994

[87] PCT Pub. No.: WO94/04497

PCT Pub. Date: Mar. 3, 1994

[30] Foreign Application Priority Data

Aug. 21, 1992 [GB] United Kingdom ............... 9217811

[51] Int. Cl.⁶ ............... C07D 213/22; C07D 401/04; C07F 15/00
[52] U.S. Cl. ............................................ 546/4
[58] Field of Search .................................. 546/4

[56] References Cited

U.S. PATENT DOCUMENTS 4,125,414  11/1978  Tang et al. ................ 136/89 NB
4,127,738  11/1978  Ghosh et al. .............. 136/89 NB
5,112,974  5/1992  Barton ........................... 546/4

OTHER PUBLICATIONS

Chemical Abstracts, vol. 90, No. 4, Abstract 29,446u, p. 384, Jan. 22, 1979.

Chemical Abstracts, vol. 87, No. 16, Abstract 125,308j, p. 522, Oct. 17, 1977.

Chemical Abstracts, vol. 95, No. 10, Abstract 88,183g, p. 479, Sep. 7, 1981.

Primary Examiner—C. Warren Ivy
Assistant Examiner—Zinna N. Davis
Attorney, Agent, or Firm—Clifford W. Browning; Woodard, Emhardt, Naughton, Moriarty & McNett

[57] ABSTRACT

A compound of formula (I): $(X)_n RuLL_1$ where n is 1 or 2, preferably 2, and in which Ru is ruthenium; each X independently is selected from Cl, SCN, $H_2O$, Br, I, CN and SeCN and L is a ligand of formulae (a) to (g) and $L_1$ is selected from a ligand of formulae (a) to (c) where each R independently is selected from OH, hydrogen, $C_{1-20}$alkyl, $-OR_a$ or $-N(R_a)_2$ and each $R_a$ independently is hydrogen or $C_{1-4}$alkyl.

6 Claims, 1 Drawing Sheet

BI-PYRIDYL-RUMETAL COMPLEXES

This application is a 371 application of PCT/EP93/02221.

The invention relates to new transition metal dyestuffs and to their use in photovoltaic cells. These dyes can be coated on titanium dioxide films rendering the device effective in the conversion of visible light to electric energy.

Titanium dioxide films (layers) are known for their semiconductive properties and this property renders them useful for photovoltaic cells. However titanium dioxide has a large band gap and therefore it does not absorb light in the visible region of the spectrum. For solar applications it is important that the titanium dioxide film be coated with a photosensitizer which harvests light in the wavelength domain where the sun emits light, i.e. between 300 and 2000 nm. Thermodynamic considerations show that conversion of solar energy into electricity is achieved in the most efficient fashion when all the emitted photons with wavelengths below 820 nm are absorbed by the photosensitizer. The optimal dye for solar conversion should therefore have an absorption onset around 800 nm and the absorption spectrum should be such that it covers the whole visible domain.

A second requirement for efficient solar light energy conversion is that the dyestuff after having absorbed light and thereby acquired an energy-rich state is able to inject with practically unit quantum yield, an electron in the conduction band of the titanium dioxide film. This requires that the dyestuff is attached to the surface of the titanium dioxide through suitable interlocking groups. The function of the interlocking group is to provide electronic coupling between the chromophoric group of the dyestuff and the conduction band of the semiconductor. This type of electronic coupling is required to facilitate electron transfer between the excited state of the dyestuff band the conduction band. Suitable interlocking groups are p-conducting substituents such as carboxylate groups, cyano groups, phosphate groups or chelating groups with p-conducting character such as oximes, dioximes, hydroxy quinolines, salicylates and alpha keto enolates. The electrons, photoinjected by the dyestuff, generate electrical current in the external circuit when the photovoltaic cell is operated.

Accordingly a new series of dyes has been developed to act as a photosensitizer.

According to the invention, there is provided a compound of formula I $$(X)_n Ru\, LL_1 \qquad (1)$$

where n is 1 or 2, preferably 2, and in which

Ru is ruthenium;

each X independently is selected from Cl, SCN, H$_2$O, Br, I, CN, —NCO and SeCN; and L is a ligand of the formula

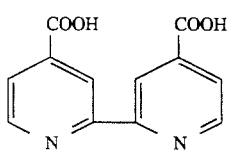

and

L$_1$ is selected from a ligand of formula a) to g)

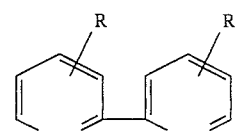 (a)

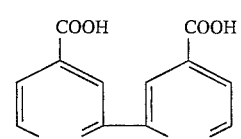 (b)

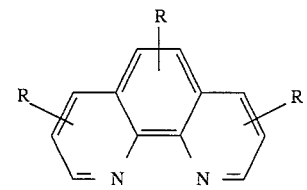 (c)

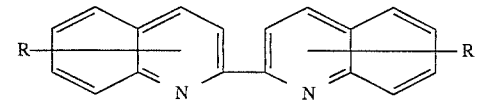 (d)

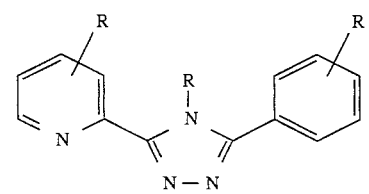 (e)

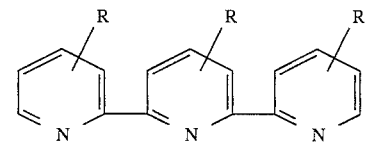 (f)

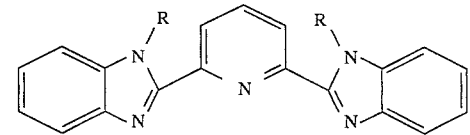 (g)

where each R independently is selected from OH, hydrogen, C$_{1-20}$alkyl, —OR$_2$ or —N(R$_a$)$_2$ and each R$_a$ independently is hydrogen or C$_{1-4}$alkyl Preferred groups of L, are those of formula a) b) c) and d).

Preferably X is X' where X' is Cl, CN, —NCO or —SCN.

Preferably L$_1$, is L$_1$', where L$_1$', is selected from a ligand of formula a', b, and c'

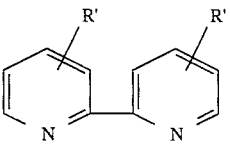 (a')

-continued

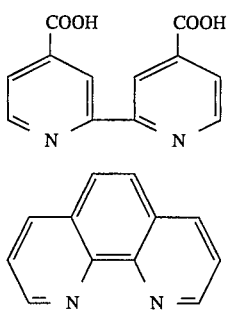

in which R' is OH, hydrogen or $C_{1-20}$alkyl, (more preferably R" where R" is hydrogen or $C_{1-20}$alkyl).

More preferred compounds of formula I are of formula II $$(X')_2RuL"L \qquad (II)$$

in which

L" a group of formula a" or b

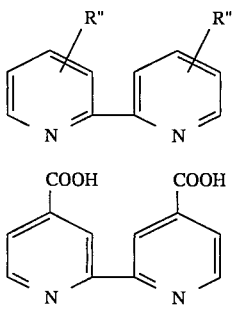

L is as defined above:

X' is selected from Cl, CN —NCO and SCN; and

R" is $C_{1-20}$alkyl (preferably $C_{1-15}$alkyl) or hydrogen

Most preferably L" is a ligand of the formula b)

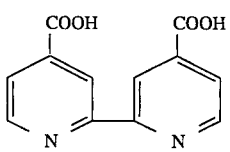

Especially preferred is cis and trans (preferably cis)-dithiocyanato-bis(2,2'-bipyridyl-4,4'-dicarboxylate)ruthenium (II).

Preferably in formulae a, a' and a", the group R and R' respectively are located in the para position to the N atom in the 4-position.

According to the invention there is provided a photovoltaic cell comprising:

an electrically conductive layer (preferably light transmitting) deposited on a support (preferably glass plate a transparent polymer sheet or a metal surface) to which one or more (preferably porous high surface area) titanium dioxide layers have been applied, characterized by applying a compound of formula I defined above (as a photosensitizer) to the TiO₂ layer.

Still further according to the invention, there is provided a photovoltaic cell comprising:

i) two electrodes, at least one of which is transparent and has a visible light transmittance of at least 60%, the plates being arranged so as to define a receptacle between them, in which receptacle an electrolyte is located, one of the electrodes having a film of titanium dioxide (preferably high surface area) the film being coated with a photosensitizer; and ii) means for permitting the passage of an electrical current generated by the cell;

characterized in that the photosensitizer is a compound of formula I defined above.

Preferably a photovoltaic cell according to the invention comprises, i) an electrically conductive first plate to which a film of titanium dioxide is applied, (the film preferably having a thickness of 0.1–50 microns) and the film being coated with a photosensitizer; and ii) a conductive second plate with no TiO₂ film separated from the first plate by a thin layer of electrolyte, whereby the visible light transmittance of at least one of the plates is at least 60%; (preferably also for solar light);

characterized in that the photosensitizer is a compound of formula I defined above.

The second plate (also known as "the counterelectrode") may be coated with a thin layer (preferably up to 10 microns thickness) of an electrocatalyst. The role of the electrocatalyst is to facilitate the transfer of electrons from the counterelectrode to the electrolyte. A further possible modification of the counterelectrode is to make it reflective to light that has first passed through the electrolyte and the first plate.

Further the outside of the glass plates may be coated with plastics like PS, PMMA or preferably PC to protect the TiO₂ layer, the dyestuff and the electrolyte against UV-light to give long term stability.

Preferably the electrolyte contains a redox system (charge transfer relay). Preferably such systems include iodine/iodide solutions, bromine/bromide solutions, hydroquinone solutions or solutions of transition metal complexes transferring a nonbonding electron. The charge transfer relays present in the electrolyte transport electric charge from one electrode to the other. They act as pure mediators and undergo no chemical alteration during the operation of the cell. It is preferable that the electrolytes in a photovoltaic cell according to the invention are dissolved in an organic medium so that the dyes applied to the titanium dioxide surface are insoluble therein. This has the advantage that the cell has a long-term stability.

Preferred organic solvents for the electrolyte include but are not limited to water, alcohols and mixtures thereof, non-volatile solvents such as 3-methyl(-2-oxazolidinone (NMO), 1,3-dimethyl-2-imidazolidinone (DMEN), propylene carbonate, ethylene carbonate and methyl pyrrolidinone, mixtures of non-volatile solvents with viscosity reducing solvents such as acetonitrile, ethylacetate or tetrahydrofuran. Additional solvents are dimethylsulfoxide or dichloroethane. Where miscible, mixtures of any of the above may be used.

Preferably the titanium dioxide films have a roughness factor greater than one, the roughness factor being defined as the ratio of true to apparent surface area. More preferably the roughness factor is 10–1000, most preferably 50–200. Preferably the titanium dioxide layers are built up on the surface of the conductive layer using the on of two methods. One, the sol-gel method is described in "Stalder and Augustynski, J. Electrochem. Soc. 1979, 126:2007" and in Application Example A. The other, the "colloidal method" is described in Application Examples B and D.

In the sol gel method it is preferable that only the last three, the last two or just the very top layer of the titanium dioxide is doped with a divalent or trivalent metal in an amount of not more than 15% doping by weight. However, the deposition of the pure dopant in form of a very thin top oxide layer can also be advantageous. In the latter cases a blocking layer is formed which impedes leakage current at the semiconductor-electrolyte junction. All of the $TiO_2$ layers are formed by the sol gel process method described in Application Example A. Preferably the number of $TiO_2$ layers deposited is 10–11. Preferably the total thickness of the $TiO_2$ film is from 5 to 50 microns (more preferably 10–20 microns).

The glass or polymer plate which is used for the transparent plate of the cell according to the invention is any transparent glass or polymer onto which a light transmitting electrically conductive layer has been deposited, such that the plate preferably has a visible light transmittance of 60–99%, more preferably 85–95%. Preferably the transparent conductive layer has a surface resistance of less than 10 ohms per square cms, preferably from 1 to 10 ohms per square cm. Preferably the transparent conductive layer used in a photovoltaic cell according to the invention is made of tin dioxide doped with ca. 0.8 atom percent of fluorine and this layer is deposited on a transparent substrate made of low-cost soda lime float glass. This type of conducting glass can be obtained from Asahi Glass Company, Ltd. Tokyo, Japan. under the brand name of TCO glass. The transparent conductive layer can also be made of indium oxide doped with up to 5% tin oxide, deposited on a glass substrate. This is available from Baizers under the brand name of ITO glass.

The photosensitising layer may be produced by applying to the $TiO_2$ layer a dye according to the invention defined below.

Cis-$(X)_2$bis(2,2'-bipyridyl-4,4'-dicarboxylate )-ruthenium(II)complexes(X=Cl,Br,CN and SCN) act as charge tranfser sensitizers for nanostructured $TiO_2$ films (thickness 8–12 μm) of very high internal surface acrea (roughness factor ca. 1000), prepared by sintering of 15–30 nm-sized colloidal titania particles on a conducting glass support. The performance of cis-dithiocyanatobis (2.2'-bipyridyl-4,4'-dicarboxylate)-ruthenium(II) is especially good. Nano-structured $TiO_2$ films coated with a mono layer of 1 μ harvest visible light very efficiently, their absorption threshold being around 800 nm. Conversion of incident photons into electric current is nearly quantitative over a large spectral range. These films can be incorporated in a thin layer regenerative solar cell equipped with a light-reflecting counterelectrode. The open circuit voltage can be increased usefully by treating the dye-covered film with 4-tert butylpyridine. The effect of temperature on the power output and long term stability of the dye is also investigated. For the first time, a device based on a simple molecular light absorber attains a conversion efficiency commensurate with that of conventional silicon based photovoltaic cells.

While tris(2,2'-bipyridyl)ruthenium(II) and it homologues have been extensively investigated as redox sensitizers, very little is known about the excited state redox properties of the bis(2,2'-bipyridyl)ruthenium(II) analogues. The reason for this is that the excited state of these compounds is often too short-lived to allow for accurence of homogeneous bimolecular electron transfer reactions. However, heterogeneous charge transfer processes might still be initiated with such sensitizers since they can take place over a very short time scale. Apart from their chemical stability and ease of interfacial charge exchange with semiconducting solids, it has been found that these complexes have a large visible light harvesting capacity which is superior to that of the widely studied trisbipyridyl Ru(II) analogues, making them useful for use in a solar energy conversion device.

One aspect of the invention relates to Ru(II) complexes having the general formula cis-$(X)_2$bis(2,2'-bipyridyl-4,4'-dicarboxylate)-ruthenium(II) complexes, where X is Cl, Br, I, CN and SCN. Among these complexes cis-dithiocyanatobis(2,2'-bipyridyl-4,4'-dicarboxylate)-ruthenium(II) displays outstanding properties as a charge transfer sensitizer. Its broad range of visible light absorption and relatively long-lived excited state renders it an attractive sensitizer for homogeneous and heterogeneous redox reactions. In conjunction with the recently developed nanostructured colloidal $TiO_2$ films and the iodide/triiodide electrolyte in a acetonitrile/3-methyl-2-oxazolidinone solvent mixture. this complex converts an appreciable amount of AM1.5 solar radiation into electrical energy approaching the performance of polycrystalline silicon photovoltaic cells.

Figure 1:
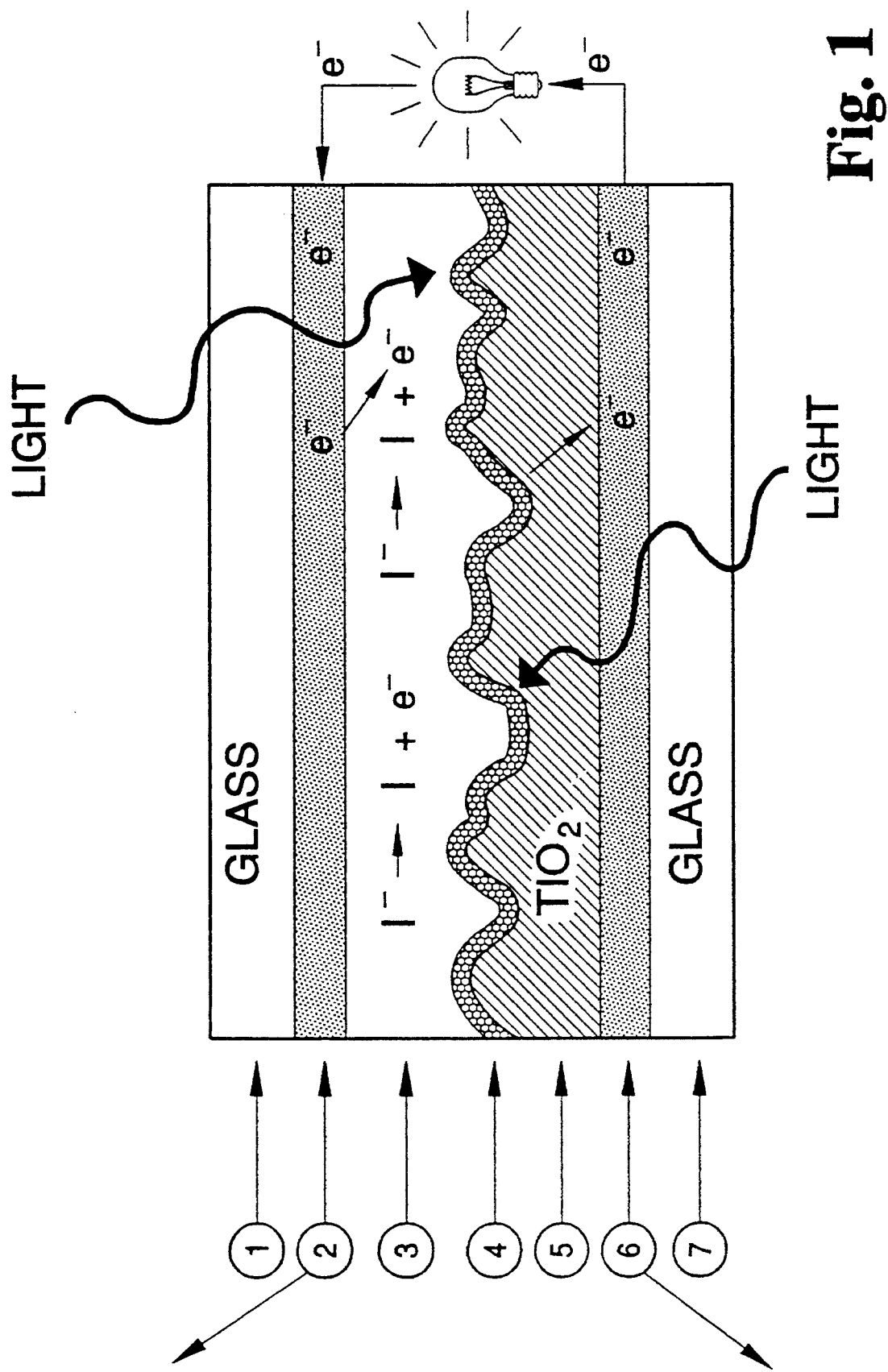
FIG. 1 is a photovoltaic device based on the sensitization of an aluminum-doped titanium dioxide film supported on conducting glass.

The invention will now be illustrated by the following Examples.

EXAMPLE 1

Preparation of Ru-bis(4,4'-COOH-2,2'-bipyridyl)-dichloride dihydrate, a compound of formula 1 a

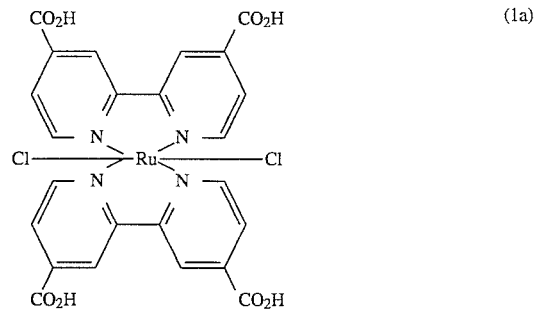

Cis—Ru(II)$L_2Cl_2$—$2H_2O$ is obtained by refluxing under Ar 60 mg (0.229 mmol) of $RuCl_3.3H_2O$(Fluka 38–40% Ru) and 113 mg (0.463 mmol) of ligand L=2,2'-bipyridyl-4,4'-dicarboxylic acid (Aldrich) in 20mL of DMF for 8 hours. After cooling, traces of $RuL_3$ are filtered. Most of the DMF solvent is evaporated under vacuum and cis-Ru(II)$L_2Cl_2$ is precipitated with acetone. The crystals are filtered off and dried in vacuum. Elemental analysis corresponds to $C_{24}H_{16}N_4O_8Cl_2Ru.2H_2O$

EXAMPLE 2

Preparation of cis-dithiocyanato-N-bis(2,2'-bipyridyl-4,4'dicarboxylic acid) ruthenium(II), dihydrate [RuL$_2$(NCS)$_2$] 2H$_2$O, a compound of formula 2a

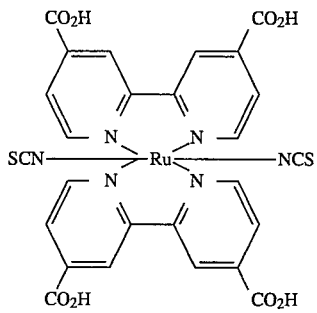

283 mg of (0.428 mmol) RuL$_2$Cl$_2$ are dissolved in 30 ml of DMF, under reduced light. 350mg (4.25 mmol) of sodium thiocyanate are separately dissolved in 2 ml of water and subsequently added to the above solution. Then the reaction mixture is heated to reflux for 6 hours under a nitrogen atmosphere, while maintaining magnetic stirring. After this time, the reaction mixture is allowed to cool and then the solvent is removed on a rotary evaporator. The resulting solid is dissolved in water and filtered through a sintered glass crucible. The pH of this filtrate is lowered to 2.5 by adding dilute HClO$_4$ or CF$_3$SO$_3$H and placed in a refridgerator over night. After allowing it to reach room temperature, the micro crystalline solid is isolated by suction filtration, washed well with water acidified with HClO$_4$ to pH3 and acetone-ether mixture (1:10) followed by anhydrous diethylether and air dried for an hour. The yield is 80%. Elemental analysis for C$_{26}$H$_{16}$N$_6$S$_2$O$_8$Ru.2H$_2$O gives (calculated values in brackets): C41.65( 42.1); H2.86 (2.272); N11.26(11.34).

Further structural characterization of 2 a can be carried out by IR spectroscopy using a DA3.26 (BOMEM Inc., Quebec, Canada) FTIR or a Perkin-Elmer 6811 instrument. The high resolution spectrum exhibits a doublet with peaks at 2126 and 2093 cm$^{-1}$ which is characteristic Of the cis-configuration of the two thiocyanate ligands. Furthermore, the N-coordination of the thiocynate group is confirmed by the presence of the v(C=S) resonance at 770 cm$^{-1}$.

EXAMPLE 3 a) Synthesis of RuCl$_2$ (DMSO)$_4$ where the DMSO=dimethylsulphoxide.

1 g of Ruthenium trichloride trihydrate is refluxed in 5ml of dimethylsulphoxide for 1 hour. After this period of time, the addition of acetone gives a yellow precipitate.

The yellow complex which separates is filtered off, washed with acetone and diethylether. The yield is about 80% b) Synthesis of RuCl$_2$(L) (DMSO)$_2$ where L is 4,4'dimethyl-2,2'bipyridine.

1 equivalent of RuCl$_2$(DMSO)$_4$, prepared above and 1 equivalent of 4,4'dimethyl-2,2'bipyridine are refluxed in chloroform for 1 hours. The solution is cooled and the solvent is removed on a rotary evaporator. The resultant solid is dissolved in acetone and filtered. Addition of diethylether to the filtrate gives a yellow precipitate. This is collected on glass frit, washed with ether and vacuum dried (giving about 80% yield).

c) Synthesis of RuLL, Cl$_2$ where L is 4,4'-dimethyl-2,2'-bipyridine and L$_1$ is 4,4'carboxy-2,2'bipyridine (hereinafter the complex of Example 3c).

1 equivalent of RuCl$_2$L (DMSO)$_2$, prepared above and 1 equivalent of 4,4'dicarboxy-2,2'-bipyridine are placed in dimthylformamide and the mixture is refluxed for 3–4 hours in the dark. After this period, the reaction mixture is filtered through sintered glass crucible. The filtrate is evaporated and the resultant solid is washed with a 1:1 mixture of acetone/ether and then washed with diethylether and vacuum dried.

EXAMPLE 4

Synthesis of RuLL,(SCN)$_2$ where L is 4,4'-dimethyl-2,2'-bipyridine and L, is 4,4'carboxy-2,2'bipyridine (hereinafter the complex of Example 4):

This is prepared by an analogous procedure to that described in Example 2 from appropriate reactants.

EXAMPLE 5 a) Synthesis of RuCl$_2$(L) (DMSO)$_2$ where L is 2,2'-bipyridine. This is prepared by an analogous procedure to that described in Example 3b from appropriate reactants b) Synthesis of RuLL, Cl$_2$ where L is 2,2'-bipyridine and L$_1$ is 4,4'carboxy-2,2'bipyridine. This is prepared by an analogous procedure to that described in 3c from appropriate reactants.

EXAMPLE 6

Synthesis of RuLL$_1$(SCN)$_2$ where L is 2,2'-bipyridine and L, is 4,4'carboxy-2,2'bipyridine.

This is prepared by an analogous procedure to that described in example 2 from appropriate reactants.

EXAMPLE 7 a) Synthesis of RuCl$_2$(L) (DMSO)$_2$ where L is 4,4'-di-C$_{13}$alkyl-2,2'-bipyridine.

This is prepared by an analogous procedure to that described in example 3b from appropriate reactants.

b) Synthesis of RuLL$_1$Cl$_2$ where L is 4,4'-di-C$_{13}$alkyl-2,2'-bipyridine and L, is 4,4'-dicarboxy-2,2'bipyridine.

This is prepared by an analogous procedure to that described in example 3c from appropriate reactants

EXAMPLE 8

Synthesis of RuLL$_1$(NCS)$_2$ where L is 4,4'-di-C$_{13}$alkyl-2, 2'-bipyridine and L$_1$ is 4,4' -dicarboxy-2,2'bipyridine.

This is prepared by an analogous procedure to that described in example 2 from appropriate reactants

EXAMPLE 9

Cis-Dicyanobis(2,2'-bipyridyl-4,4'-dicarboxylic acid) ruthenium(ll)trihydrate is synthesized by dissolving 235 mg (3.6 mmol) of KCN in 10 ml of H$_2$O and transferring it into a three-neck flask containing 30 ml of DMF. Subsequently, 500 mg (0.76 mmol) of RuL$_2$Cl$_2$.2H$_2$O of Example 1 are introduced into the above solution. The reaction mixture is then heated to reflux under nitrogen for 5 hours. During this period, the initially violet color of the solution changes to orange. After this time, the reaction mixture is allowed to cool and then filtered through a glass frit. The filtrate is evaporated to dryness on a rotary evaporator and the resulting solid is dissolved in H$_2$O at pH 10. Upon addition of dilute HClO$_4$ or CF$_3$SO$_3$H to the above solution, most of the complex precipitates as a neutral salt at pH 2–3. The orange solid is isolated by suction filtration, washed well with $H_2O$, ethyl alcohol, followed by anhydrous diethylether and air dried for an hour. The yield is 70%.

EXAMPLE 10

Synthesis of [Ru L $(PPh_3)_2(Cl)_2$] where L is selected from the ligands 4,4-dicarboxy-2,2-bipyridine (the ligand of formula b).

This is prepared by analogous procedure to that described in example 3b from appropriate reactants, using low or high boiling organic solvents. Most preferable solvent is acetone.
Ph=phenyl

EXAMPLE 11

Synthesis of [$RuLL_1(Cl)_2$] where L is selected from the ligand of formula b and $L_1$ is 4,4 COOH-2,2-bipyridine.

This is prepared by analogous procedure to that described in example 3c from appropriate reactants, using low or high boiling organic solvents. Most preferably solvent is N,N-dimethylformamide.

EXAMPLE 12

Synthesis of [$RuLL_1(NCS)_2$] where L is selected from the ligand of formula b) and $L_1$ is 4,4 COOH2,2-bipyridine.
This is prepared by an analogous procedure to that described in example 2 from appropriate reactants.

EXAMPLE 13 a) Synthesis of [$Ru(CO)_2(Cl)_n$] where n is 2 or 3.

Ruthenium trichloride (1 gr) is refluxed with 90% formic acid until the solution changes from green to yellow over 3–4 hours. The solution is then filtered and evapored on the steam bath to give the bright a yellow product, having yield of 90%.

b) Synthesis of [Ru L $(CO)_2(Cl)_2$] where L is selected from the ligand of formula (b).

This is prepared by analogous procedure to that described in example 3b using low or high boiling solvents. Most preferable solvent is EtOH or MeOH. When appropriate reactants i.e. the compound of example 13a and the ligand b) are heated at reflux in MeOH for 15 to 60 minutes, the yellow solid precipitates and is isolated as a fine yellow crystals having yield of 90%.

c) Synthesis of [$RuLL_1(Cl)_2$] where L and $L_1$ are 4,4-COOH-2,2-bipyridine.

This is prepared by analogous procedure to that described in example 3c from appropriate reactants, i.e. the compound of example 13b and 4,4-COOH-2,2-bipyridine using low or high boiling organic solvents. Most preferable solvent is N,N-dimethylformamide.

EXAMPLE 14

Synthesis of [$RuLL_1(NCS)_2$] where L and $L_1$ are 4,4-COOH-2,2-bipyridine.

This is prepared by an analogous procedure to that described in example 2 from appropriate reactants i.e. the compound of example 13c and NaNCS.

EXAMPLE 15

Synthesis of [$RuLL_1Cl_2$] where L is 4,4 -COOH-2,2-bipyridine and $L_1$ is selected from the group of formula (c), where R is hydrogen.

EXAMPLE 16

Synthesis of [$RuLL_1Cl_2$] where L is 4,4-COOH-2,2-bipyridine and $L_1$ is selected from the group of formula (d), where R is hydrogen.

EXAMPLE 17

Synthesis of [$RuLL_1Cl_2$] where L is 4,4-COOH-2,2-bipyridine and $L_1$ is selected from the group of formula (e), where R is hydrogen.

These compounds i.e. example 15, 16 and 17 can be prepared by an analogous procedure to that described in example 3c from appropriate reactants.

EXAMPLE 18 a) Synthesis of [$RuL_1(Cl)_3$].

1 equivalent of Ruthenium trichloride and 1 equivalent of $L_1$ [where $L_1$ is selected from the ligand of the formula (f) or (g) where R is hydrogen] are refluxed in EtOH for 30 to 60 minutes. After this period, the resulting solid was collected on G4 crucible and washed with EtOH.

b) Synthesis of [$RuLL_1Cl$] where L is 4,4-COOH2,2-bipyridine and $L_1$ is selected from the group of formula (f) where R is hydrogen.

This is prepared by refluxing 1 equivalent of [$RuL_1(Cl)_3$] and 1 equivalent of L in DMF for 3 to 5 hours. After allowing to room temperature, the solvent DMF is evaporated and the resulted solid is dissolved in water. The pH of this solution is adjusted to 2.5 by diluted $HClO_4$, which give a dense precipitate. This precipitate is collected on crucible and washed with water acidified with $HClO_4$ to pH 3 and acetone-ether mixture followed by anhydrous diethyl ether. The product was air dried for 2 hours.

EXAMPLE 19

Synthesis of [$RuLL_1Cl$] where L is 4,4-COOH-2,2-bipyridine and $L_1$ is selected from the group of formula (g) where R is hydrogen.

This is prepared by an analogous procedure to that described in example 18b from appropriate reactants i.e. the compound of formula 18a and 4,4-COOH-2,2-bipyridine.

Application Example A

A photovoltaic device shown in FIG. 1 and based on the sensitization of an aluminum-doped titanium dioxide film supported on conducting glass is fabricated as follows:

A stock solution of organic titanium dioxide precursor is prepared by dissolving 21 mmol of freshly distilled $TiCl_4$ in 10 mL of absolute ethanol. $TiCl_4$ in ethanol solution gives titanium alkoxide spontaneously which, on hydrolysis, gives $TiO_2$ The stock solution is then diluted with further absolute ethanol to give two solutions (solution A and solution B having) titanium contents of 25 mg/ml (solution A) and 50 mg/ml (solution B). A third solution (C) is prepared from solution B by addition of $AlCl_3$ to yield an aluminium content of 1.25 mg/ml. A conducting glass sheet provided by Asahi Inc. Japan, surface area 10 $cm^2$ and having a visible light transmittance of at least 85% and a surface resistance smaller than 10 ohms per square cm is used as support for a deposited $TiO_2$ layer. Prior to use, the glass is cleaned with alcohol. A droplet of solution A is spread over the surface of the conducting glass to produce a thin coating. Subsequently the layer is hydrolyzed at 28° C. for 30 minutes in a special chamber, where the humidity is kept at 48% of the equilibrium saturation pressure of water. Thereafter, the electrode is heated in air in a tubular oven kept at 450° C., preheating it in the entrance of the oven for 5 minutes followed by 15 minutes of heating in the interior. Three more layers are produced in the same way. Subsequently, 5 thicker layers are deposited by using solution B. The same procedure as for the first layers is applied. Finally, solution C is used to deposit the last two layers containing the aluminum dopant. The heating of the last layer in the tubular oven is extended from 15 to 30 minutes. The total thickness of the titanium dioxide film is between 10 and 20 microns.

Prior to deposition of the dye, the film is subjected to a sintering treatment in highly purified 99.997% argon. A horizontal tubular oven composed of quartz tubes with suitable joints is employed. After insertion of the glass sheet with the $TiO_2$ film, the tube is twice evacuated and purged with argon. The glass sheet is then heated under argon flux at a flow rate of 2.5L/h and a temperature gradient of 500° C./h up to 550° C. at which temperature it maintained for 35 minutes. This treatment produces anatase films with a surface roughness factor of 80–200.

After cooling under a continuous argon flow, the glass sheet is immediately transferred to an alcoholic solution (or alcoho/dimethylsulfoxide mixture) of a chromophore. The chromophore employed is the complex of Example 2. Its concentration in absolute ethanol is $5 \times 10^{-4}$M. Prolonged exposure of the film to the open air prior to dye adsorption is avoided in order to prevent hydroxylation of the $TiO_2$ surface as the presence of hydroxyl groups at the electrode surface interferes with dye uptake. The adsorption of chromophore from the ethanolic solution is allowed to continue for 30 minutes after which time the glass sheet is withdrawn and washed briefly with absolute ethanol. The $TiO_2$ layer on the sheet assumed a deep red colour owing to the chromophore coating.

The photocurrent action spectrum obtained with such a film using a conventional three electrode electrochemical cell containing an ethanolic solution of 0.5M LiI and $3 \times 10^{-3}$M iodine is shown in the attached figure together with the AM 1 spectral distribution of solar light emission. The incident monochromatic photon to current conversion efficiency (IPCE) is plotted as a function of the excitation wavelength. This was derived from the equation:

$$IPCE (\%) = \frac{[(1.24 \times 10^3) \times \text{photocurrent density } (\mu A/cm^2)]}{[\text{wavelength (nm)} \times \text{photon flux } (W/m^2)]} \quad (1)$$

From the overlap of the photocurrent action spectrum with solar emission the overall efficiency for the conversion of solar light to electricity η is calculated from the formula $$\eta = 12 \times OCV \times FF(\%) \quad (2)$$

where OCV is the open circuit voltage and FF is the fill factor of the photovoltaic cell.

For experimental verification of equation 2, a photovoltaic cell, shown in the drawing attached, is constructed, using the dye of Example 1 (4)-loaded $TiO_2$ (5) film supported on a conducting glass (the working electrode) comprising a transparent conductive tin dioxide layer (6) and a glass substrate (7) as a photoanode. The cell has a sandwich-like configuration, the working electrode (4–7) being separated from the counter electrode (1,2) by a thin layer of electrolyte (3) having a thickness of ca. 20 microns. The electrolyte used is an ethanolic solution of 0.5M LiI and $3 \times 10^{-3}$M iodine. The electrolyte (3) is contained in a small cylindrical reservoir (not shown) attached to the side of the cell from where capillary forces attract it to the inter-electrode space. The counter-electrode comprises the conductive tin dioxide layer (2) deposited on a glass substrate (1) made also of Asahi conducting glass and is placed directly on top of the working electrode. A monomolecular transparent layer of platinum is deposited on to the conducting glass of the counter electrode (1,2) by electroplating from an aqueous hexachloroplatinate solution. The role of the platinum is to enhance the electrochemical reduction of iodine at the counter electrode. The transparent nature of the counterelectrode is an advantage for photovoltaic applications since it allows the harvesting of light from both the forward and the backward direction. Experiments are carried out with a high pressure Xenon lamp equipped with appropriate filters to simulate AM1 solar radiation. The intensity of the light is varied between 50 and 600 Watts per square meter and the open circuit voltage is 660 and 800 mV, respectively at these two voltages. The fill factor defined as the maximum electric power output of the cell divided by the product of open circuit voltage and short circuit current is between 0.7 and 0.75 V. A single crystal silicon cell gave an open voltage of 550 mV at 600 W/m² incident light intensity which dropped to below 300 mV at 50 W/m². This clearly shows that the cell of the present invention has a higher open circuit voltage than the silicon solar cell and that the open circuit voltage is less dependent on light intensity than that of the silicon cell. This constitutes a significant advantage for the use of such a cell in indirect sunlight or cloudy weather conditions. The fill factor of the silicon cell is comparable to that of the example. The overall solar light to electricity conversion efficiency of the cell of the example is between 5 and 6% in agreement with predictions of equation 2.

Application Example B

A transparent $TiO_2$ film from colloidal titanium dioxide particles which are deposited on a conducting glass support and sintered to yield a coherent highly porous semiconducting film that is transparent and can be used instead of the $TiO_2$ layer film in Application Example A.

Colloidal titanium oxide particle of approximately 10 nm are prepared by hydrolysis of titanium isopropoxide as follows:

125 ml of titanium isopropoxide is added to a solution of 0.1M nitric acid in 750 ml of water whilst stirring. A precipitate of amorphous titanium dioxide is formed under these conditions. This is heated to 80° C. for approximately 8 hours, stirring vigorously, resulting in peptisation of the precipitate and formation of a clear solution of colloidal anatase. The anatase structure of the titanium dioxide particles is established by Raman spectroscopy. The sol is concentrated by evaporation of the solvent in vacuum at room temperature until a viscous liquid is obtained containing the colloidal particles. At this stage the nonionic surfactant TRITON X-100 (40% weight of $TiO_2$) is added to reduce cracking of the film when applied to a substrate.

The titanium dioxide films are formed by spin coating the concentrated sol on to a conducting glass substrate. Usually it is sufficient to apply 6 to 10 layers in order to obtain semiconductor membranes of sufficient surface area to give excellent visible light harvesting efficiencies after deposition of a monolayer of the sensitizer.

Low resolution electron microscopy confirms the presence of the three layer structure, the lowest being the glass support followed by the 0.5 micron thick fluorine-doped $SnO_2$ and the 2.7 micron thick titanium dioxide layer. High resolution electron microscopy reveals the $TiO_2$ film to be composed of a three dimensional network of interconnected particles having an average size of approximately 16 nm. Apparently, significant particle growth occurs during sintering.

The transparent $TiO_2$ films are tested in conjunction with a sensitizer, the dye of Example 2 regenerative cell for the generation of electricity from visible light. The results can be represented where the photocurrent under simulated sunlight (intensity ca 30 W/m$^2$) is plotted as a function of cell voltage.

Application Example C

A sheet of conducting glass (ASAHI) area resistance ca 10 Ohm/square cm) having a size of 2×9.6 cm$^2$ is coated with a colloidal titanium dioxide film according to the procedure of Example B. A total of 7 layers of $TiO_2$ colloid are deposited successively by spin coating and the film is subjected each time to calcination at 500° C. for 30 minutes. 30% (w/w) of TRITON X 405 surfactant is added in order to avoid cracking of the film.

The final thickness of the titanium dioxide film is 5 microns as determined from the optical interference pattern. It is important to note that the conducing glass sheet after deposition of the $TiO_2$ remains clear and transparent to visible and near infrared light. The transmission spectrum recorded on a conventional spectrophotometer shows that a fraction of more that 60% of the visible light in the wavelength region between 400 and 900 nm is transmitted through the film. A UV/visible absorption spectrum of the electrode can be obtained. It exhibits a flat feature in the visible due to light absorption and scattering by the conducting glass and the 5 nm thick $TiO_2$ film. The steeply rising part of the absorption below 400 nm is due to the band gap absorption of the $TIO_2$.

Immediately before coming with dyestuff, the film is fired for 1 hour at 500° C. The coating of $TiO_2$ with dyestuff is performed by immersing the glass sheet for 16 hours in an ethanolic (or alcohol/diemthylsulfoixde mixture) solution containing the complex of Example 2. After coating, the glass sheet displays an intensive dark reel coloration. The optical absorption spectrum measured with a conventional UV/visible spectrophotometer shows the absorbance in the vicinity of 500 nm to exceed the value of 2, indicating that in this wavelength range more than 99% of the photons are absorbed by the dyestuff deposited on to the titanium dioxide film. It is important to note that, due to the high concentration of dyestuff, the porous film is capable of harvesting photons over a very broad spectral range extending from 450 to 850 nm.

After dye deposition, the glass sheet is cut into two parts each having a size of ca 9 cm$^2$. These sheets serve as working electrodes (photo-anodes) in the module whose assembly is described further below.

Transparent counterelectrodes are made of the same type of ASAHI conducting glass as the working electrodes. The counterelectrode is not coated with $TiO_2$. Instead, the equivalent of 10 monolayers of Pt is electrochemically deposited on to conducting glass. The transparent nature of the counterelectrode is not affected by the deposition of the Pt its transmission in the visible and near infrared remaining greater that 60%. The Pt acts as an electrocatalyst, enhancing the rate of reduction of the electron transfer mediator, i.e. triiodide, at the counterelectrode. Two ca. 1 mm deep and 1.5 mm wide and 20 mm long indentations are engraved into the surface of the counterelectrode close to the edges of the glass sheets. These serve as a reservoir for the electrolyte.

The counter electrode is placed directly on top of the working electrode to yield a sandwich-type configuration. After filling the reservoirs with electrolyte, the cell was sealed with epoxy resin. The wetting of the space between the two electrodes by the electrolyte occurs spontaneously by capillary action. The electrolyte is a solution of 0.5M tetrapropyl ammonium iodide and 0.02M iodine in ethanol.

Two cells are fabricated in this way, each having a surface area of ca 9cm$^2$. Subsequently they are connected in series by electrically contacting the photoanode of one cell to the cathode of the second cell. In this way a module is constructed, having a total surface area of 18cm$^2$.

Application Example D

Nanostructured $TiO_2$ films are prepared by spreading a viscous dispersion of colloidal $TiO_2$ particles on a conducting glass support (Asahi TCO glass, fluorine-doped $SnO_2$ overlayer, transmission ca 85% in the visible, sheet resistance 8 Ohm/square cm) and subsequent heating under air for 30 min at 30°–450° C. (preferably 450° C.). Two methods of preparation of colloidal $TiO_2$ dispersions are employed.

a) The procedure of Application Example C is repeated except that autoclaving is performed at 230° to 240° C. instead of 500° C. After spreading the colloid on the conducting glass support and calcining, a few monolayers of $TiO_2$ are electrodeposited onto the colloidal $TiO_2$ film from an aqueous Ti(III) solution followed by renewed annealing at 450° C. This treatment is found to improve significantly the short circuit photocurrent as well as the open circuit voltage of the solar cell. Low resolution electron microscopy confirms the presence of a three-layer structure, the lowest being the glass support followed by the 0.7 μm thick fluorine-doped $SnO_2$ and the 10 μm thick colloidal $TiO_2$ film. High resolution electro microscopy reveals the $TiO_2$ film to be composed of a three-dimensional network of interconnected particles having an average size of approximately 15 nm.

b) The second method for preparation of nanosturctured films (Method B) employed commercial $TiO_2$ (P25, Degussa AG, Germany, a mxiture of ca 30% rutile and 70% anatase). This is produced by flame hydrolysis of $TiCl_4$ and consists of weakly aggregated particles. The BET surface areas is 55 m$^2$/g, corresponding to a mean particle size of about 25 nm. In order to break the aggregates into separate particles, the powder (12g) is ground in a porcelain mortar with a small amount of water (4 ml), containing acetylacetone (0.4 ml) to prevent reaggregation of the particles. Other stabilizers such as acids, bases or $TiO_2$ chelating agents are found to be suitable as well. After the powder has been dispersed by the high shear forces in the viscose paste it is diluted by slow addition of water (16 ml) under continued grinding. Finally, a detergent (0.2 ml Triton®X-100) is added to facilitate the spreading of the colloid on the substrate. The conducting TCO glass is covered on two parallel edges with adhesive tape (~40 μm thick) to control the thickness of the $TiO_2$ film and to provide noncoated area for electrical contact. The colloid (5 μl/cm$^2$) is applied to one of the free edges of the conducting glass and distributed with a glass rod sliding over the tape covered edges. After air drying, the electrode is fired for 30 minutes at 30°–550° C. (preferably 450°–550° C.) in air. The resulting film thickness is 12 μm but can be varied by changing the colloid concentration or the adhesive tape thickness.

The performance of the film, as sensitized photoanode, is improved by further deposition of $TiO_2$ from aqueous $TiCl_4$ solution. A 2M $TiCl_4$ stock solution is prepared at 0° C. to prevent precipitation of $TiO_2$ due to the highly exothermic hydrolysis reaction. This stock solution is freshly diluted with water to 0.2M $TiCl_4$ and applied onto the electrode (50 μl/$cm_2$). After standing overnight at room temperature in a closed chamber, the electrode is washed with distilled water. Immediately before dipping into the dye solution it is fired again for 30 minutes at 30°–550° C. (preferably 450-550° C.) in air. Similarly to the electro-deposition from aqueous Ti(III) solution, this procedure results in the deposition of nano-sized $TiO_2$ particles on the $TiO_2$ film further increasing its active surface area. Furthermore, this treatment as well as the anodic deposition of $TiO_2$ from Ti(III) solution described above appears to lead to deposits having a very low impurity content. This is corroborated by the fact that the treatment becomes ineffective if the $TiCl_4$ solution is evaporated before firing instead of being washed off. Impurities in the $TiCl_4$, such as $Fe^{3+}$, are not deposited by hydrolysis from the acidic $TiCl_4$ solution due to the higher solubility of iron oxide compared to $TiO_2$. By contrast, the evaporation of the $TiCl_4$ solution results in the deposition of impurities. The P25 powder contains up to 100 ppm $Fe_2O_3$, which is known to interefere with electro-injection of the excited dye. The $TiC_4$ treatment covers this rather impure core with a thin layer of highly pure $TiO_2$ improving the injection efficiency and the blocking character of the semi-conductor-electrolyte junction.

Coating of the $TiO_2$ surface with dyestuff is carried out by soaking the film for ca 3h in a $3\times10^{-4}$M solution of the ruthenium complex from Example 1 in dry ethanol (or alcohol/dimethylsulfoxide mixture). The dye coating is done immediately after the high temperature annealing in order to avoid rehydroxylation of the $TiO_2$ surface or capillary condensation of water vapor from ambient air inside the nanopores of the film. The presence of water in the pores decreases the injection efficiency of the dye. The electrode is dipped into the dye solution while it is was still hot, i.e. its temperature is ca 80° C. After completion of the dye adsorption, the electrode is withdrawn from the solution under a stream of dry air or argon. It is stored in dry ethanol or immediately wetted with the LiI/ILiI$_3$ acetonitrile redox electrolyte for testing. The amount of adsorbed dye is determined by desorbing the dye from the $TiO_2$ surface into a solution of $10^{-4}$ NaOH in ethanol (or alcohol/dimethyl-sulfoxide mixture) and measureing its adsorption spectrum.

A BAS-100 electrochemical analyzer (Bioanalytical Systems, USA) is used to perform cyclic voltammetry in electrochemical cells of columes of 5 to 20 ml. A three-electrode cell is made up of a glassy carbon or Pt disc (3mm diameter embedded in Teflon) working electrode and a platinum wire counter electrode. The reference electrode consists of calomel in contact with 0.1 LiCl in methanol. It is separated from the working electrode compartment by bridge containing the same electrolyte as the test solution, i.e. 0.1M n-tetrabutylammonium perchlorate in acetonitrile or ethanol. All potentials indicated refer to the aqeueous SCE electrode.

Photo-electrochemical experiments are employed a similar cell equipped with a flat pyrex window. Alternatively, the dye sensitized $TiO_2$ film is incorporated into a thin layer sandwich type solar cell. A light reflecting counterelectrode is employed consisting of a conducting glass support onto which a 2 μm thick Pt mirror had been deposited by sputtering. The counterelectrode is placed directly on top of the dye coated transparent $TiO_2$ film supported by the conducting glass sheet. Both electrodes are clamped tightly together. A thin layer of electrolyte is attracted into the inter-electrode space by capillary forces. The dyed coated $TiO_2$ film is illuminated through the conducting glass support. The conversion efficiencies reported are overall yields which are uncorrected for losses due to light absorption and reflection by the conducting glass support. An Oriel 450 W Xe lamp served as a light source in conjunction with a polycarbonate filter to remove ultraviolet radiation and a Schott a 113 interference filter to mimic AM 1.5-type solar emission.

The emission spectra are measured on a Spex Ruorolog II equipped with a 450 W Xenon light source. The measured excitation and emission spectra are routinely corrected for the wavelength-dependent features using correction factors generated by a National Bureau of Standards 150 W halogen lamp. The emission detector is a Hamamatsu R2658 photomultiplier which extends the corrected emission measurement over a region from 250 to 1000 nm. All solutions are prepared by dissolving the appropriate amount of complex in the desired solvent to give typically a $2\times10^{-5}$M solution. The solutions are degassed by freeze, pump and thaw methods. Low temperature measurements are carried out in an Oxford Instruments cryostat.

The emission lifetimes are measured by exciting the sample with active modelocked Nd YAG laser pulse, using the frequency doubled line at 532 nm. The emission decay is followed on a Tektronix DSA 602 A Digitizing Signal Analyzer. The digitized xy data is subsequently analyzed and fitted to an exponential model. Sample concentrations were typically $1\times10^{-4}$M. Optical densities are taken from spectra recorded on a Cary 5 spectrophotometer.

Application Example E

A photovoltaic device shown in FIG. 1 based on the sensitization of a transparent $TiO_2$ film made from colloidal titanium dioxide particles which are deposited on a conducting glass support and sintered to yield a coherent highly porous semiconducting film.

Colloidal titanium oxide particles of approximately 8 nm are prepared by hydrolysis of titanium isopropoxide as follows:

125 ml titanium isopropoxide is added to a solution of 0.1M nitric acid in 750 ml water while stirring. A precipitate of amorphous titanium dioxide is formed under these conditions. This is heated to 80° C. for approximately 8 hours, stirring vigorously, resulting in peptisation of the precipitate and formation of a clear solution of colloidal anatase. The propanol formed by the hydrolysis is allowed to evaporate during the heating. The colloidal solution is then autoclaved at 230° to 240° C., in a pressure vessel of titanium metal or teflon for 2 to 20 hours, preferably 16 hours. The resultant sol, containing some precipitate is stirred or shaken to resuspend the precipitate. The resulting sol, minus any precipitate that will not resuspend, is concentrated by evaporation of the solvent in vacuum at room temperature until a viscous liquid is obtained containing the colloidal particles. A typical concentration at this point is 200 g/L. At this stage a polyethylene oxide polymer, for example Union Carbide Carbowax 20M or Triton X-405 can be added to increase the thickness of the layer that be deposited without cracks. The polymer is added in amount of 30 to 50, preferably 40, weight percent $TiO_2$.

The electrodes for sensitization are formed from the colloidal solution as follows:

A suitable substrate, for example a 3×6 cm piece of conductive tin oxide coated glass, for example from Asahi Corp. (but also titanium metal or any flat conductive surface), is placed with the conductive surface up and with suitable spacers, for example 50 to 100 micron, preferably 80 micron thick plastic tape, placed along each edge. A suitable amount of the sol, for example 150 microliters of sol with 200 g/L $TiO_2$ and 40% Carbowax 20M for the above substrate, is pipetted along one end of the substrate. The sol is spread across the substrate by drawing with a flat edged piece of glass whose ends ride along the spacers. Thus the spacers, the viscosity of the sol, and the concentration of the sol control the amount of $TiO_2$ deposited. The as spread film is allowed to dry in room air till visibly dry and preferable and additional 20 minutes. After drying the electrode is fired at 400° to 500° C., preferably 450, for a minimum of 20 minutes. In the case of sols autocraved below 170° C. the spacers less than 40 micron must be used and the process must be repeated twice to achieve an 8 to 10 micron thick $TiO_2$ film.

Electrodes of up to 10 cm by 10 cm have been fabricated by this method. The sol can also be applied to substrates by spin coating and dip coating.

The electrode can then be cut to the size desired by normal glass cutting techniques. Immediately before applying the sensitizer the electrode is fired again at 450 to 550, preferably 500° C. for 2 to 12, preferably 6 hours. For some solvent and dye combinations the surface of the electrode is improved (with respect to electron injection ) by firing the electrode 5 to 10, preferably 7 times at 500° C. for 2 to 6 hours with either 10 hours in air or soaking up to 1 hour in water, 0.5M nitric acid or 0.5M HCl, between each firing. The acid solutions are saturated with dissolved $TiO_2$ before use. After the last firing, immediately after cooling, the electrode is placed in the sensitizer solution. Preferably an ethanolic (or alcohol/dimethylsulfoxide mixture) solution containing the complex of Example 1 is made up. Depending on the sensitizer between 4 and 24 hours are required for the electrode to gain full color. Full color can be estimated by eye or by taking visible light transmittance spectra of the dye at various time.

After removal form the dye solution, the electrode is made into a photovoltaic cell as follows:

Transparent counterelectrodes are made of the same type of ASAHI conducting glass as the working electrodes. The counterelectrode is not coated with $TiO_2$. Instead the equivalent of 10 monolayers of Pt is electrochemically deposited onto conducting glass. The transparent nature of the counterelectrode is not affected by the deposition of the Pt, its transmissions is visible and near infrared remains greater that 60%. The Pt acts as an electrocatalyst enhancing the rate of reduction of the electron transfer mediator, i.e. triiodide, at the counterelectrode. Alternatively, a thin titanium sheet, which may be porous coated as above with Pt, may be used as a counter electrode. In the case of a porous sheet, another sheet of impervious material is required behind the counter electrode, such as plastic. glass or metal.

A reservoir is provided for the electrolyte by engraving two ca 1 mm deep and 1.5 mm wide and 20 mm long clefts into the surface of the counterelectrode close to the edges of the glass sheet. The reservoir can also be added external to the glass sheets or be behind the counter electrode in the case of porous counter electrode.

The countereletrode is place directly on top of the working electrode to yield a sandwich type configuration. The reservoirs are filled with electrolyte solution, selected from the list above buy preferably 85% by weight ethylene carbonate, 15% propylene carbonate 0.5M potassium iodide and 40 mM iodine. An amount of LiI or tetraalkylammonium iodide can be present (preferably 20 mM) depending on the voltage desire. The cell is sealed around the edge with a sealant compatible with the solvent chosen and bonded closed with an adhesive. The sealant and the adhesive may be the same material for example silicon adhesive in the case of the alcohol solvents, or for example,polyethylene and epoxy resin (or mechanical closure) in the case of ethylene carbonate. The wetting of the space between the two electrodes by the electrolyte injected into the reservoirs occurs spontaneously by capillary action.

Application Examples A to E can be repeated using instead to the compound of Example 2, the same amount of the 4,4-dicarboxy- or 4,4-dialkyl-bipyridyl ruthenium dyes of Examples 1 and 3 to 19.

We claim:

1. A compound of formula I $$(X)_n Ru\, LL_1 \qquad (I)$$

where n is 1 or 2 and

Ru is ruthenium;

each X independently is selected from Cl, SCN, $H_2O$, Br, I, CN, —NCO and SeCN;

and

L is a ligand of the formula

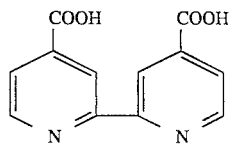

and $L_1$ is selected from a ligand of formula a) to g)

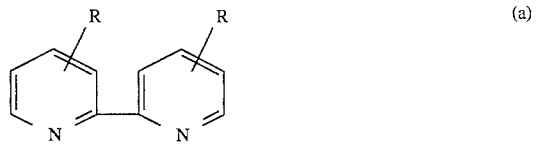

(a)

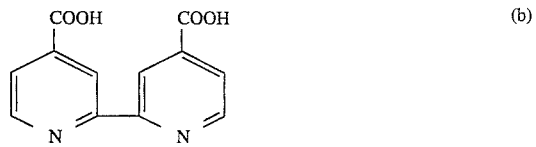

(b)

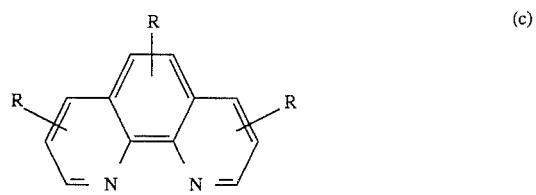

(c)

-continued

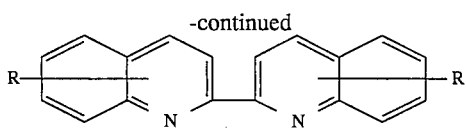
(d)

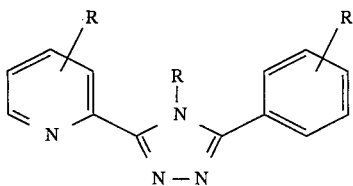
(e)

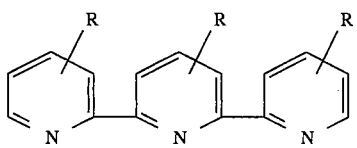
(f)

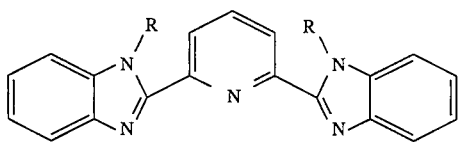
(g)

where
- each R independently is selected from OH, hydrogen, $C_{1-20}$alkyl, $-OR_a$ or $-N(R_a)_2$
and
- each $R_a$ independently is hydrogen or $C_{1-4}$alkyl.

2. A compound according to claim 1 in which X is X' where X' is —Cl, CN, —NCO or —SCN.

3. A compound according to claim 1 in which $L_1$ is $L_1'$ where $L_1'$ is selected from a ligand of formula a', b, and c'

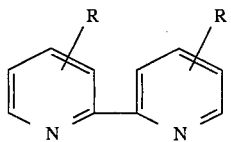
(a')

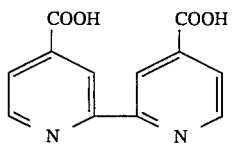
(b)

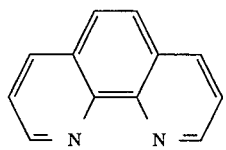
(c')

in which R' is OH, hydrogen or $C_{1-20}$alkyl.

4. A compound of formula II $$(X')_2 Ru(L'')_2 \qquad (II)$$

in which

L'' is a group of formula a'' or b

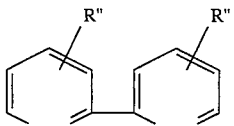
(a'')

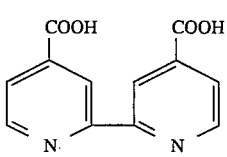
b)

and

X' is selected from Cl, NCO, CN and SCN; and

R'' is hydrogen or $C_{1-20}$alkyl.

5. A compound according to claim 2 in which $L_1$ is $L_1'$ where $L_1'$ is selected from a ligand of formula a', b, and c'

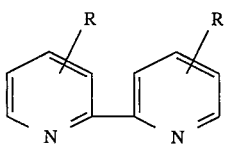
(a')

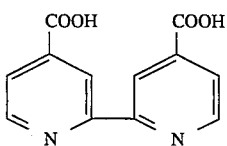
(b)

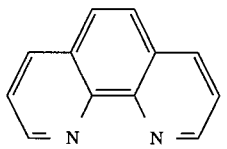
(c')

in which R' is OH, hydrogen or $C_{1-20}$alkyl.

6. A compound according to claim wherein said compound is selected from cis or trans-dithiocyanato-bis(2,2'-bipyridyl-4,4'-dicarboxylate)ruthenium and cis-dithiocyanato-bis(2,2'-bipyridyl- 4,4'-dicarboxylate)ruthenium.

* * * * *

UNITED STATES PATENT AND TRADEMARK OFFICE
CERTIFICATE OF CORRECTION

PATENT NO. : 5,463,057

DATED : October 31, 1995

INVENTOR(S) : Michael Graetzel, Mohammad K. Nazeeruddin

It is certified that error appears in the above-identified patent and that said Letters Patent is hereby corrected as shown below:

In column 13, line 37 please delete "coming" and insert in lieu thereof --coating--.

In column 13, line 42, please delete "reel" and insert in lieu thereof --red--.

In column 15, line 11, please delete "$\mu l/cm_2$" and insert in lieu thereof --$\mu l/cm^2$--.

In column 20, line 50, please insert --4-- between the words "claim" and "wherein".

Signed and Sealed this

Second Day of July, 1996

BRUCE LEHMAN

Attest:

Attesting Officer

Commissioner of Patents and Trademarks